(12) United States Patent
Takahashi et al.

(10) Patent No.: US 11,224,763 B2
(45) Date of Patent: Jan. 18, 2022

(54) TRACKING DEVICE FOR RADIATION TREATMENT, POSITION DETECTION DEVICE, AND METHOD FOR TRACKING MOVING BODY

(71) Applicant: Shimadzu Corporation, Kyoto (JP)

(72) Inventors: Wataru Takahashi, Kyoto (JP); Shota Oshikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/627,148

(22) PCT Filed: Dec. 27, 2017

(86) PCT No.: PCT/JP2017/046856
§ 371 (c)(1),
(2) Date: Dec. 27, 2019

(87) PCT Pub. No.: WO2019/003474
PCT Pub. Date: Jan. 3, 2019

(65) Prior Publication Data
US 2020/0155870 A1    May 21, 2020

(30) Foreign Application Priority Data

Jun. 30, 2017    (WO) .................. PCT/JP2017/024214

(51) Int. Cl.
*A61N 5/10*     (2006.01)
*A61B 6/12*     (2006.01)

(52) U.S. Cl.
CPC .............. *A61N 5/1049* (2013.01); *A61B 6/12* (2013.01); *A61N 2005/1061* (2013.01)

(58) Field of Classification Search
CPC .......... A61N 5/1049; A61N 2005/1061; A61N 5/1067; A61B 6/12; A61B 6/487
See application file for complete search history.

(56) References Cited

U.S. PATENT DOCUMENTS 5,943,435 A * 8/1999 Gaborski ............. G06K 9/6292
                                                             382/132
6,307,914 B1    10/2001 Kunieda et al.
(Continued)

FOREIGN PATENT DOCUMENTS

JP    H4-52873 A    2/1992
JP    2001-511372 A    8/2001
(Continued)

OTHER PUBLICATIONS

Written Opinion of International Search Authority for PCT/JP2017/046856 (dated Apr. 10, 2018) (submitted with partial translation).

(Continued)

*Primary Examiner* — Marcus H Taningco
(74) *Attorney, Agent, or Firm* — Muir Patent Law, PLLC

(57) ABSTRACT

A control part 30 includes: a DRR image creation part 31 that creates a DRR image including a specific site; a specific site projection part 32 that creates a projection region image representing the region of the specific site; a discriminator learning part 33 that learns a discriminator for recognizing the region of the specific site by performing machine learning with use of the DRR image and the projection region image as a training label image; a specific site region detection part 34 that detects the region of the specific site by performing discrimination using the discriminator learned by the discriminator learning part 33 on an X-ray fluoroscopic image including the specific site; and a radiation signal generation part 35 that transmits a treatment beam radiation signal to an irradiation device 90 when the region of the specific site detected by the specific site region detection part 34 is included in the radiation region of a treatment beam.

17 Claims, 12 Drawing Sheets

(56) References Cited

U.S. PATENT DOCUMENTS

| | | | |
|---|---|---|---|
| 2010/0246915 A1* | 9/2010 | Yamakoshi | A61B 6/032 382/131 |
| 2013/0279780 A1* | 10/2013 | Grbic | A61B 8/5276 382/131 |
| 2015/0223773 A1* | 8/2015 | John | A61B 6/503 600/424 |
| 2016/0175614 A1 | 6/2016 | Taguchi et al. | |
| 2017/0360325 A1* | 12/2017 | Hebert | G06T 7/269 |

FOREIGN PATENT DOCUMENTS

| | | |
|---|---|---|
| JP | 3053389 B1 | 4/2004 |
| JP | 2007-279967 A | 10/2007 |
| JP | 2011-14051 A | 1/2011 |
| JP | 2016-99668 A | 5/2016 |
| JP | 2016-116659 A | 6/2016 |

OTHER PUBLICATIONS

First Japanese Office Action dated Jul. 6, 2021 for the corresponding Japanese Patent Application No. 2019-526128, submitted with a machine translation.
Second Office Action dated Nov. 9, 2021 issued for the corresponding Japanese Application No. 2019-526128.

* cited by examiner

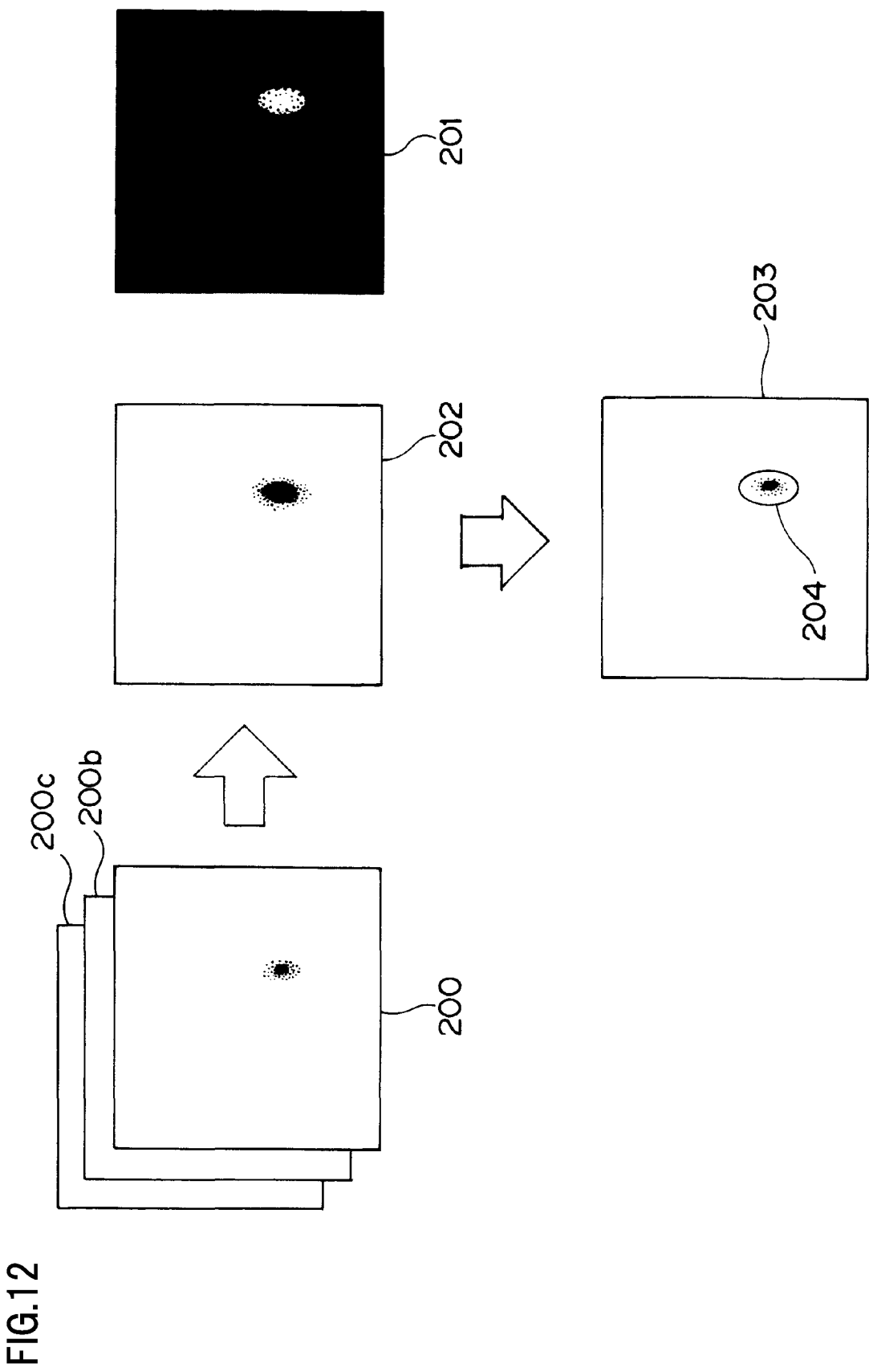

TRACKING DEVICE FOR RADIATION TREATMENT, POSITION DETECTION DEVICE, AND METHOD FOR TRACKING MOVING BODY

TECHNICAL FIELD

The present invention relates to a tracking device for radiation treatment, a position detection device, and a method for tracking a moving body, which from an image including a specific cite of a subject, detect the position of the specific cite or track the movement of the specific site.

BACKGROUND ART

In radiation treatment that radiates a radiation beam such as an X-ray beam or a proton beam as a treatment beam to an affected area such as a tumor, it is necessary to accurately radiate the radiation beam to the affected area. However, in addition to the case where the subject moves the body, the affected area itself may move. For example, a tumor in the vicinity of a lung greatly moves on the basis of breathing. For this reason, there has been proposed an irradiation device of a marker tracking type, which is configured to place a metallic marker having a spherical shape in the vicinity of a tumor, and detect the position of the marker using an X-ray fluoroscope to control the timing to radiate a treatment beam (see Patent Literature 1).

In such an irradiation device, the marker placed in the body is imaged using a first X-ray fluoroscopic mechanism including a first X-ray tube and a first X-ray detector and a second X-ray fluoroscopic mechanism including a second X-ray tube and a second X-ray detector, and a two-dimensional fluoroscopic image by the first X-ray fluoroscopic mechanism and a two-dimensional fluoroscopic image by the second X-ray fluoroscopic mechanism are used to obtain three-dimensional positional information. In addition, X-ray fluoroscopy is continuously performed, and the three-dimensional positional information on the marker is calculated in real time to thereby detect the marker in the moving site with high accuracy. Further, by controlling the timing to radiate the treatment beam on the basis of the detected positional information on the marker, highly accurate irradiation responding to the movement of the tumor can be performed. When obtaining the positional information on the marker, template matching using templates is performed.

Meanwhile, as described above, in order to detect the movement of a tumor using a marker, it is necessary to preliminarily place the marker in the body of a subject. On the other hand, in recent years, there has been proposed a method called markerless tracking, which omits the placement of a marker by using a specific site such as a patient's tumor region instead of a marker.

CITATION LIST

Patent Literature

[Patent Literature 1]
Japanese Patent No. 3053389

SUMMARY OF INVENTION

Technical Problem

In the markerless tracking that uses a specific site of a subject instead of a spherical marker, the recognized shape of the specific site differs depending on a breathing phase of the subject, and therefore even when a template is created using an image obtained by imaging the specific site at a single breathing phase, this is not enough to perform accurate template matching. For this reason, in order to respond to the fact that the recognized shape of the specific site differs depending on a breathing phase of the subject, it is necessary to store multiple images including the specific site imaged at different breathing phases just before radiation treatment as template images and perform template matching on images obtained by imaging at regular time intervals with use of the preliminarily stored multiple template images.

When using multiple templates as described, an operator has to fluoroscope a subject with X-rays just before radiation treatment to specify the position of a tumor at each breathing phase while viewing an X-ray image, and create the templates. For this reason, there is caused a problem that it takes time to create the multiple templates, which is not only painful to a patient but causes a reduction in throughput for the treatment.

When the above-described marker tracking method is employed, a point-like marker is tracked, whereas when the markerless tracking is employed, a specific site having a predetermined size itself is tracked. However, a conventional tracking method has been configured to calculate the position of any one point in the specific site, such as the center of the specific site, but not one directly taking account of the region of the specific site. In contrast, a region to which a treatment beam is radiated is registered as a region having a certain size, and for the specific site as well, it is desirable to take account of the region of it.

On the other hand, to track a specific site, it has also been proposed to use another tracking method instead of the template matching, such as machine learning. In such a case, it is conceivable to use a sliding window in CNN (convolutional neural network). However, the sliding window in CNN is easy in implementation but requires performing very redundant calculation, and therefore has the problem that the calculation takes time to make it difficult to perform real-time processing.

Meanwhile, a specific site such as a tumor changes its shape while moving in association with breathing or the like even during treatment. Also, when performing radiation treatment, fractionated radiation that radiates a treatment beam multiple times is often performed, and the repeated radiation may result in a change in shape, such as a reduction in the size of the tumor. In such a case, unless the region of the tumor can be recognized in real time in response to the change in the tumor shape, the radiation treatment cannot be performed with high accuracy.

The present invention has been made in order to solve the above-described problems, and intends to provide a tracking device for radiation treatment, a position detection device, and a method for tracking a moving body, which are capable of detecting or tracking the position of a specific site in real time by preliminarily learning a discriminator using DRR images and training label images and performing discrimination using the discriminator and X-ray fluoroscopic images.

Solution to Problem

A first aspect of the present invention is a tracking device for radiation treatment, which collects an X-ray fluoroscopic image including a specific site of a subject, detects the position of the specific site, and tracks the movement of the specific site in order to radiate a treatment beam to the specific site, and the tracking device includes: a DRR image creation part that creates a DRR image including the specific site by performing virtual fluoroscopic projection simulating geometrical fluoroscopic conditions between an X-ray tube and an X-ray detector with respect to the subject on CT image data on a region including the specific site, which created at the time of treatment planning; a discriminator learning part that learns a discriminator for recognizing the region of the specific site by performing machine learning with use of the DRR image created by the DRR image creation part and a training label image indicating the region of the specific site; and a specific site region detection part that detects the region of the specific site by performing discrimination using the discriminator learned by the discriminator learning part on an X-ray fluoroscopic image including the specific site.

A second aspect of the present invention further includes a specific site projection part that creates a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at the time of the treatment planning, in which the discriminator learning part learns the discriminator with, as the training label image, the projection region image representing the region of the specific site, which is created by the specific site projection part.

A third aspect of the present invention is such that the DRR image creation part creates the DRR image with parameters including at least one of a projection coordinate and an angle among the geometrical fluoroscopic conditions changed or image processing including at least one of rotation, deformation, and scaling of an image performed, the specific site projection part creates the projection region image representing the region of the specific site with parameters including at least one of a projection coordinate and an angle among the geometrical fluoroscopic conditions changed or image processing including at least one of rotation, deformation, and scaling of an image performed, and the DRR image creation part and the specific site projection part change parameters including at least one of a projection coordinate and an angle among the geometrical fluoroscopic conditions under the same condition, or perform image processing including at least one of rotation, deformation, and scaling of an image under the same condition.

A fourth aspect of the present invention is such that the DRR image creation part performs at least one of contrast change, noise addition, and edge enhancement on the created DRR image.

A fifth aspect of the present invention is such that the discriminator learning part learns a discriminator that is a neural network configured of a convolution layer with the DRR image as an input layer and a label image representing the region of the specific site as an output image.

A sixth aspect of the present invention is such that when calculating a loss function for performing the machine learning, the discriminator learning part performs the calculation after increasing the weight of a specific site label on the basis of areas of the specific site label and a background label in the training label image, and then performs the calculation while sequentially decreasing the weight of the specific site label as the learning progresses.

A seventh aspect of the present invention is such that when calculating a loss function for performing the machine learning, the discrimination learning part weights a loss function for an image obtained by trimming the periphery of the specific site and adds the resulting loss function to a loss function for the entire image.

An eighth aspect of the present invention further includes an image processing part that performs image processing of the DRR image and the X-ray fluoroscopic image, in which the discriminator learning part performs the machine learning with use of the DRR image and a DRR image after the image processing by the image processing part, and the specific site region detection part performs the discrimination using the discriminator learned by the discriminator learning part on the X-ray fluoroscopic image including the specific site and an X-ray fluoroscopic image that includes the specific site and was subjected to the image processing by the image processing part under the same condition as for the DRR image.

A ninth aspect of the present invention is a position detection device that detects the position of a specific site on the basis of an X-ray fluoroscopic image including the specific site of a subject, and the position detection device includes: a DRR image creation part that creates a DRR image including the specific site by performing virtual projection simulating geometrical fluoroscopic conditions between an X-ray tube and an X-ray detector with respect to the subject on CT image data on a region including the specific site; a discriminator learning part that learns a discriminator for recognizing the region of the specific site by performing machine learning with use of the DRR image created by the DRR image creation part and a training label image indicating the region of the specific site; and a specific site region detection part that detects the region of the specific site by performing discrimination using the discriminator learned by the discriminator learning part on an X-ray fluoroscopic image including the specific site.

A tenth aspect of the present invention further includes a specific site projection part that creates a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at the time of treatment planning, in which the discriminator learning part learns the discriminator with, as the training label image, the projection region image representing the region of the specific site, which is created by the specific site projection part.

An eleventh aspect of the present invention is such that the DRR image creation part creates the DRR image with parameters including at least one of a projection coordinate and an angle among the geometrical fluoroscopic conditions changed or image processing including at least one of rotation, deformation, and scaling of an image performed, the specific site projection part creates the projection region image representing the region of the specific site with parameters including at least one of a projection coordinate and an angle among the geometrical fluoroscopic conditions changed or image processing including at least one of rotation, deformation, and scaling of an image performed, and the DRR image creation part and the specific site projection part change parameters including at least one of a projection coordinate and an angle among the geometrical fluoroscopic conditions under the same condition, or perform image processing including at least one of rotation, deformation, and scaling of an image under the same condition.

A twelfth aspect of the present invention is such that the DRR image creation part performs at least one of contrast change, noise addition, and edge enhancement on the created DRR image.

A thirteenth aspect of the present invention is such that the discriminator learning part learns a discriminator that is a neural network configured of a convolution layer with the DRR image as an input layer and a label image representing the region of the specific site as an output image.

A fourteenth aspect of the present invention is such that when calculating a loss function for performing the machine learning, the discriminator learning part performs the calculation after increasing the weight of a specific site label on the basis of areas of the specific site label and a background label in the training label image, and then performs the calculation while sequentially decreasing the weight of the specific site label as the learning progresses.

A fifteenth aspect of the present invention is such that when calculating a loss function for performing the machine learning, the discriminator learning part weights a loss function for an image obtained by trimming the periphery of the specific site and adds the resulting loss function to a loss function for an entire image.

A sixteenth aspect of the present invention further includes an image processing part that performs image processing of the DRR image and the X-ray fluoroscopic image, in which the discriminator learning part performs the machine learning with use of the DRR image and a DRR image after the image processing by the image processing part, and the specific site region detection part performs the discrimination using the discriminator learned by the discriminator learning part on the X-ray fluoroscopic image including the specific site and an X-ray fluoroscopic image that includes the specific site and was subjected to the image processing by the image processing part under the same condition as for the DRR image.

A seventeenth aspect of the present invention is a method for tracking a moving body, which collects an X-ray fluoroscopic image including a specific site of a subject, detects the position of the specific site, and tracks the movement of the specific site in order to radiate a treatment beam to the specific site, and the method includes: a DRR image creation step of creating a DRR image including the specific site by performing virtual fluoroscopic projection simulating geometrical fluoroscopic conditions between an X-ray tube and an X-ray detector with respect to the subject on CT image data on a region including the specific site, which is created at the time of treatment planning; a specific site projection step of creating a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at the time of the treatment planning; a discriminator learning step of learning a discriminator for recognizing the position of the specific site by performing machine learning with use of the DRR image created in the DRR image creation step and the projection region image created in the specific site projection step; and a specific site region detection step of detecting the region of the specific site by performing discrimination using the discriminator learned in the discriminator learning step on an X-ray fluoroscopic image including the specific site, which is obtained by detecting an X-ray passing through the subject after radiation from the X-ray tube with use of the X-ray detector.

Advantageous Effects of Invention

According to the first and seventeenth aspects of the present invention, the position of the specific site can be detected or can be tracked in real time by, before the radiation treatment, preliminarily learning a discriminator and performing discrimination with use of the discriminator and an X-ray fluoroscopic image. At this time, the need to preliminarily prepare templates as conventional is eliminated, and therefore a patient does not suffer because the need to prepare multiple templates is eliminated. In addition, throughput for treatment can be improved.

According to the second and tenth aspects of the present invention, since the discriminator is learned with the projection region image representing the region of the specific site, which is created by performing the virtual fluoroscopic projection on the region of the specific site registered on the CT image data on the region including the specific site, as the training label image, a label image can be accurately and easily created.

According to the third and eleventh aspects of the present invention, since parameters including a projection coordinate and an angle among the geometrical fluoroscopic conditions are changed or image processing including the rotation, deformation, and/or scaling of an image is performed, the position of the specific site can be accurately detected even when the specific site is moved or deformed unreproducibly. In addition, a large number of DRR images can be created, and therefore a custom-made discriminator corresponding to each patient can be learned, and further even when a DRR image created from low frame rate CT image data is used, or even when a background is imaged superimposed on the specific site, the position of the specific site can be accurately detected.

According to the fourth and twelfth aspects of the present invention, since the contrast change, noise addition, and/or edge enhancement is performed on the created DRR image, the position of the specific site can be accurately detected even when the DRR image and the X-ray image differ in image quality.

According to the fifth and thirteenth aspects of the present invention, since the discriminator that is the neural network configured of a convolution layer with the DRR image as an input layer and a label image representing the region of the specific site as an output image is learned, the need for redundant calculation is eliminated, and real-time processing can be performed.

According to the sixth and fourteenth aspects of the present invention, when calculating a loss function for the machine learning, the specific site label and the background label can be equivalently handled, and the specific site can be more surely detected. In addition, in the former half of the learning, the discriminator is learned so that the specific site can be surely detected, and in the latter half of the learning, the learning is performed so as to prevent the background part from being erroneously determined, so that the discriminator satisfying both the detection reliability of the specific site and the suppression of the erroneous detection can be learned.

According to the seventh and fifteenth aspects of the present invention, the weight of the vicinity of a difficult-to-discriminate boundary between the specific site label and the background label can be increased to perform the learning, and this makes it possible to suppress the erroneous determination of the vicinity of the boundary between the specific site label and the background label and more surely detect the specific site.

According to the eighth and sixteenth aspects of the present invention, a discriminator with higher accuracy can be created, and the region of the specific site can be more accurately detected.

According to the ninth aspects of the present invention, the position of the specific site can be detected in real time by, before the radiation treatment, preliminarily learning a discriminator with use of the DRR image and a training label image, and performing discrimination with use of the discriminator and an X-ray fluoroscopic image.

BRIEF DESCRIPTION OF DRAWINGS

FIG. 9 is a schematic diagram illustrating an X-ray fluoroscopic image 200, label images 201, 202 representing the region of the specific site, and the like.

FIG. 12 is a schematic diagram illustrating an X-ray fluoroscopic image 200, images 200b, 200c after image processing of it, and label images 201, 202 representing the region of the specific site, and the like

DESCRIPTION OF EMBODIMENTS

Figure 1:
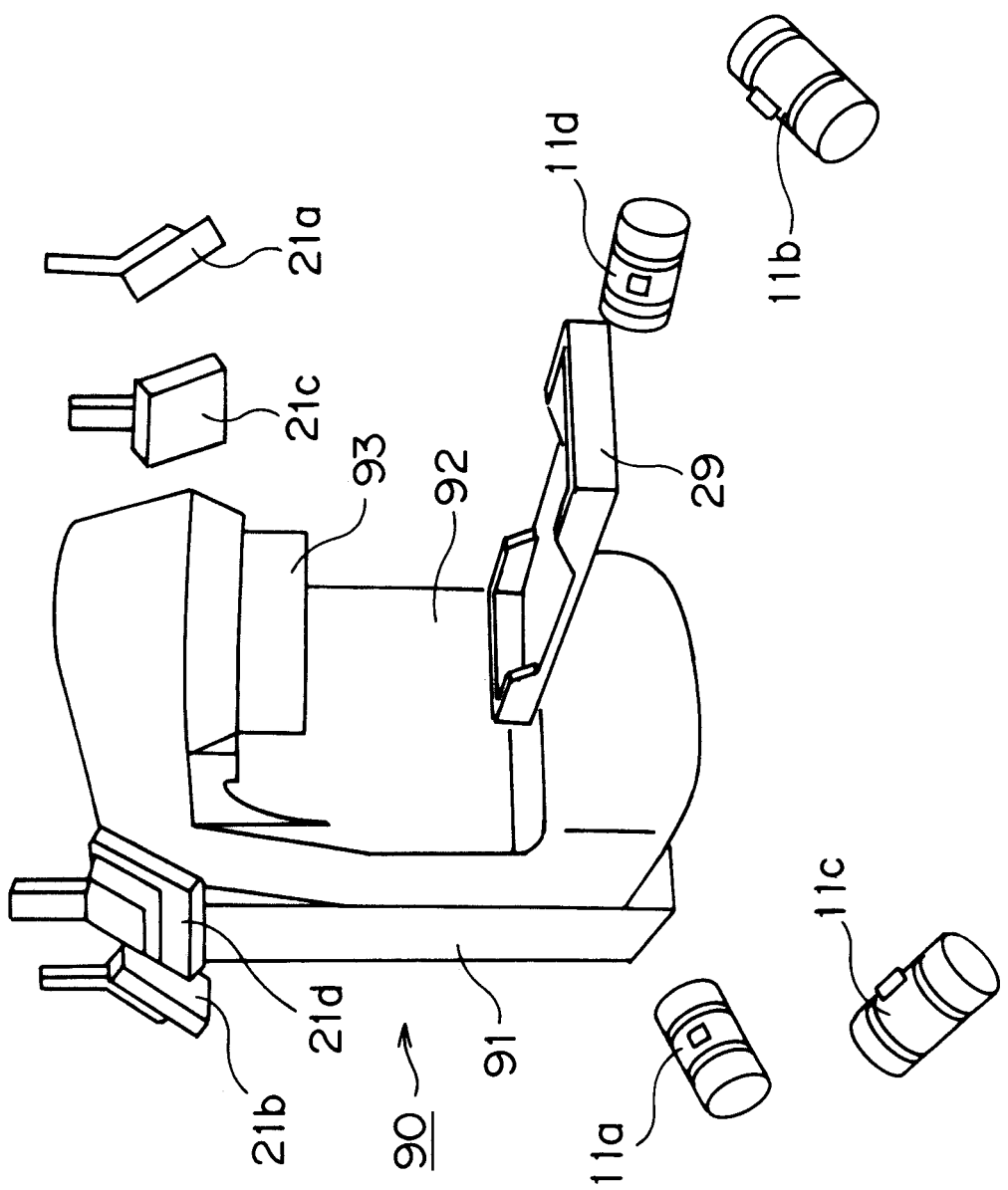
FIG. 1 is a perspective view illustrating the tracking device for radiation treatment according to the present invention together with an irradiation device 90.

In the following, embodiments of the present invention will be described on the basis of the drawings. FIG. 1 is a perspective view illustrating the tracking device for radiation treatment according to the present invention together with an irradiation device 90. The tracking device for radiation treatment and the irradiation device 90 constitute a radiation treatment device.

The irradiation device 90 is one that performs irradiation on a subject on an examination table 29 called a couch, and includes: a gantry 92 installed swingably with respect to a base 91 installed on a floor surface of a treatment room; and a head 93 that disposed on the gantry 92 and emits a treatment beam. In the irradiation device 90, the gantry 92 swings with respect to the base 91, and thereby the radiation direction of the treatment beam radiated from the head 93 can be changed. For this reason, the treatment beam can be radiated to an affected area of the subject, such as a tumor, from various directions.

The tracking device for radiation treatment used together with the irradiation device 90 is an X-ray fluoroscopic device that performs X-ray fluoroscopy for performing moving body tracking for specifying the position of the affected area of the subject. That is, during radiation treatment using the above-described irradiation device 90, the radiation beam has to be accurately radiated to the affected area that moves along with the body movement of the subject. For this purpose, it is configured to detect the specific site with high accuracy, i.e., perform so-called moving body tracking by preliminarily registering a subject's site having a specific shape, such as a tumor, as a specific site, and continuously fluoroscoping the specific site with X-rays to calculate three-dimensional positional information on the specific site. As described, a moving body tracking method that, instead of placing a marker in the vicinity of an affected area of a subject in a conventional manner, uses an image of the subject's specific site such as a tumor as a marker is called markerless tracking.

The tracking device for radiation treatment includes a first X-ray tube 11a, second X-ray tube 11b, third X-ray tube 11c, fourth X-ray tube 11d, first flat panel detector 21a, second flat panel detector 21b, third flat panel detector 21c, and fourth flat panel detector 21d. X-rays radiated from the first X-ray tube 11a are transmitted through the subject on the examination table 29 and then detected by the first flat panel detector 21a. The first X-ray tube 11a and the first flat panel detector 21a constitute a first X-ray imaging system. X-rays radiated from the second X-ray tube 11b are transmitted through the subject on the examination table 29 and then detected by the second flat panel detector 21b. The second X-ray tube 11b and the second flat panel detector 21b constitute a second X-ray imaging system. X-rays radiated from the third X-ray tube 11c are transmitted through the subject on the examination table 29 and then detected by the third flat panel detector 21c. The third X-ray tube 11c and the third flat panel detector 21c constitute a third X-ray imaging system. X-rays radiated from the fourth X-ray tube 11d are transmitted through the subject on the examination table 29 and then detected by the fourth flat panel detector 21d. The fourth X-ray tube 11d and the fourth flat panel detector 21d constitute a fourth X-ray imaging system.

In addition, when performing X-ray fluoroscopy for performing the moving body tracking, or when performing X-ray imaging for imaging the specific site of the subject, two X-ray imaging systems among the first X-ray imaging system, second X-ray imaging system, third X-ray imaging system, and fourth X-ray imaging system are selected and used.

Figure 2:
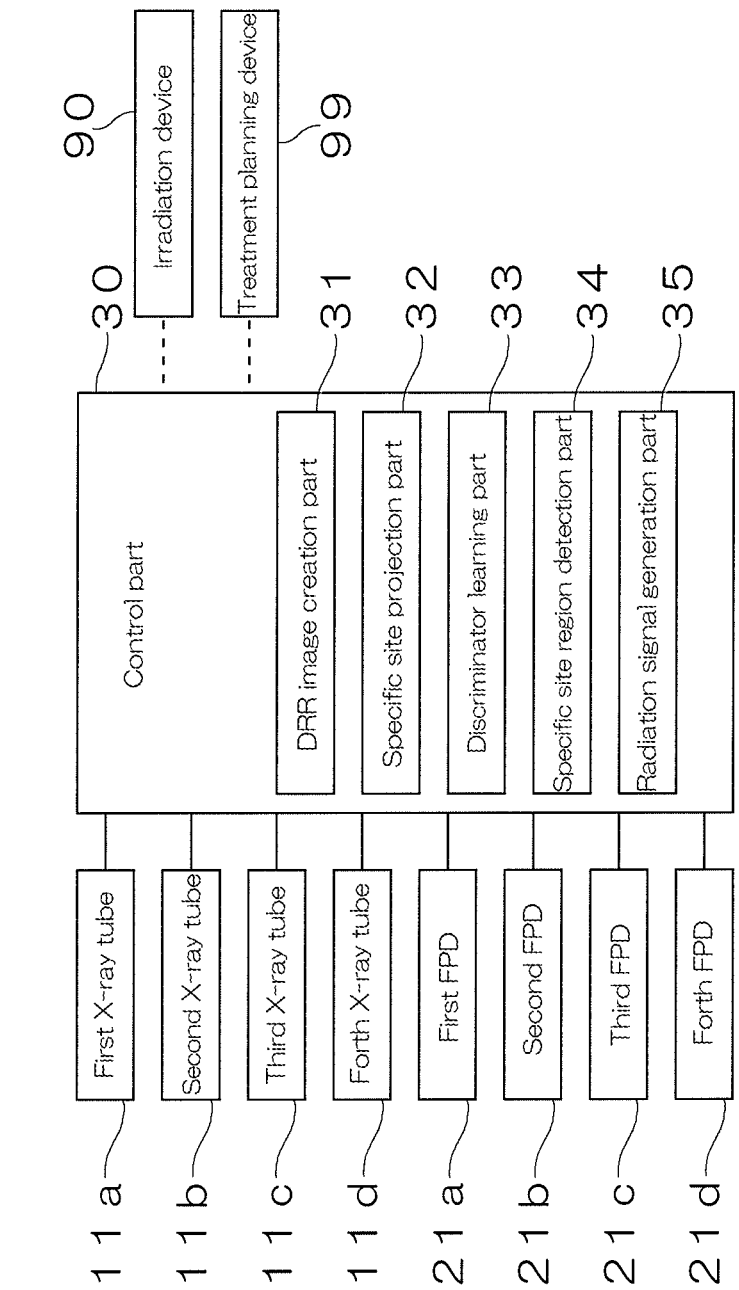
FIG. 2 is a block diagram illustrating a main control system of the tracking device for radiation treatment according to the present invention.

FIG. 2 is a block diagram illustrating a main control system of the tracking device for radiation treatment according to the present invention.

The tracking device for radiation treatment includes: a CPU as a processor for performing logical operations; an ROM in which an operation program necessary to control the device is stored; an RAM in which data or the like is temporarily stored at the time of control, and the like, and includes a control part 30 that controls the entire device. The control part 30 is connected to the above-described first X-ray tube 11a, second X-ray tube 11b, third X-ray tube 11c, fourth X-ray tube 11d, first flat panel detector 21a, second flat panel detector 21b, third flat panel detector 21c, and fourth flat panel detector 21d.

As described below, the control part 30 includes: a DRR image creation part 31 that creates a DRR image including the specific site by performing virtual fluoroscopic projection simulating the geometrical fluoroscopic conditions between the X-ray tubes 11 and the flat panel detectors 21 with respect to the subject on CT image data that is created at the time of treatment planning and on a region including the specific site; a specific site projection part 32 that creates a projection region image representing the region of the specific site by performing the virtual fluoroscopic projection simulating the geometrical fluoroscopic conditions between the X-ray tubes 11 and the flat panel detectors 21 with respect to the subject on the region of the specific site registered on the CT image data on the region including the specific site at the time of the treatment planning; a discriminator learning part 33 that learns a discriminator for recognizing the region of the specific site by performing machine learning using the DRR image created by the DRR image creation part 31 and the projection region image as a training label image; a specific site region detection part 34 that detects the region of the specific site by performing discrimination using the discriminator learned by the discriminator learning part 33 on X-ray fluoroscopic images including the specific site obtained by detecting X-rays transmitted through the subject after radiation from the X-ray tubes 11 by the flat panel detectors 21; and a radiation signal generation part 35 that transmits a treatment beam radiation signal to the irradiation device 90 when the region of the specific site detected by the specific site region detection part 34 is included in the radiation region of the treatment beam.

Also, the control part 30 is connected to the above-described irradiation device 90 and a treatment planning device 99. In addition, the control part 30 and the treatment planning device 99 may be connected via a radiology information system (RIS) that is in-hospital communication for a subject management system in a hospital. Further, the treatment planning device 99 is one for creating a treatment plan before performing radiation treatment. The treatment planning device 99 stores four-dimensional CT image data consisting of a group of pieces of three-dimensional CT image data on the region including the specific site at multiple continuous breathing phases of the subject, which are obtained by using a CT imaging device to continuously perform three-dimensional CT imaging on the subject multiple times. In addition, a treatment plan for the subject is created on the basis of the four-dimensional CT image data and other pieces of data on the subject.

When creating the treatment plan, CT image data on the region including the specific site is provided with information on the region of the specific site and then stored. The information on the region of the specific site is given by, for example, an operator. The information on the region of the specific site may be adapted to be automatically given by another method.

Next, an operation for performing the moving body tracking that detects the position of the specific site moving along with the body movement of the subject and tracks the movement of it by using the tracking device for radiation treatment having a configuration as described above will be described.

Figure 3:
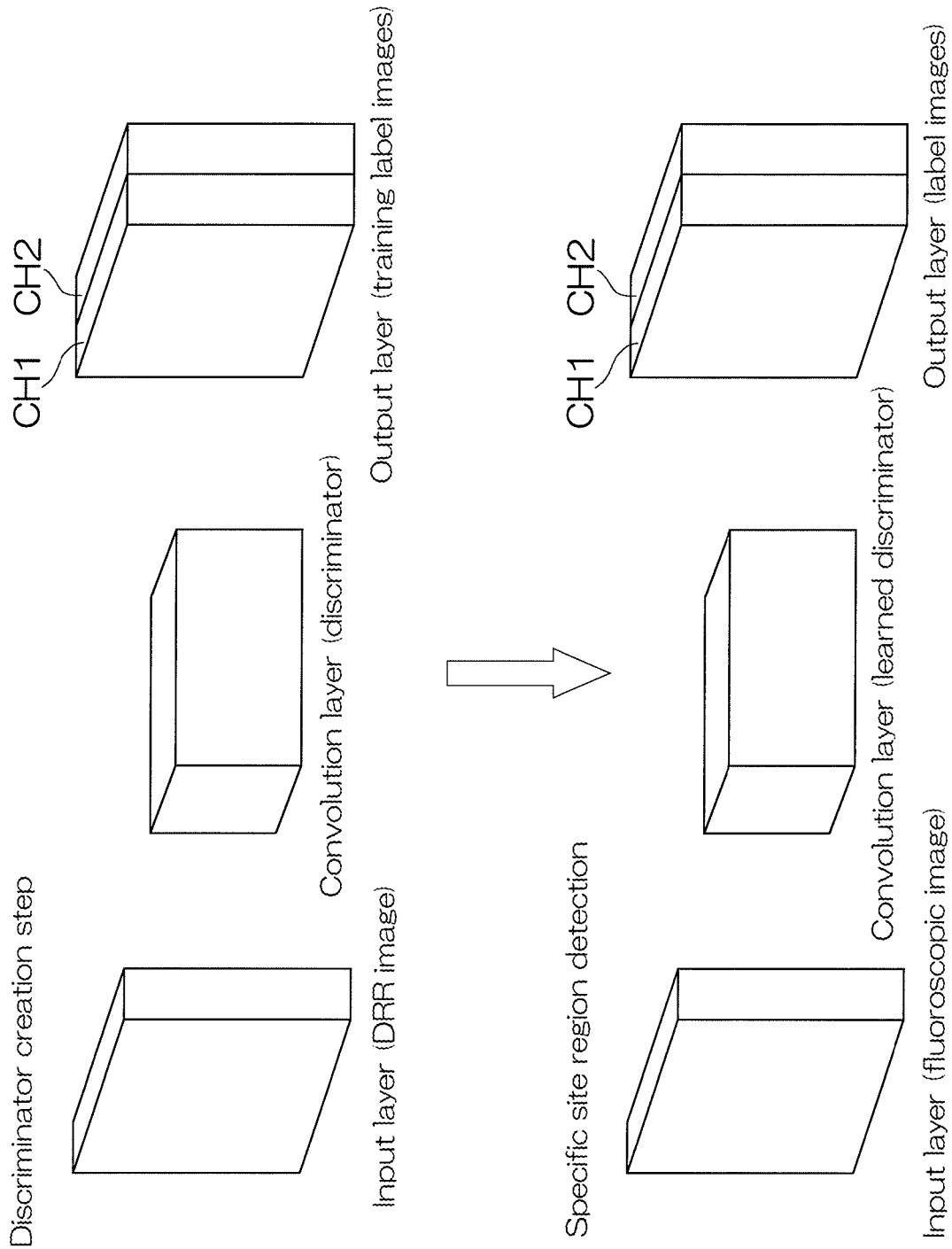
FIG. 3 is a schematic diagram for explaining steps of using machine learning to detect the position of a region of a specific site by the tracking device for radiation treatment according to the present invention.

First, the basic concept for detecting the position of the specific site will be described. FIG. 3 is a schematic diagram for explaining steps of using machine learning to detect the position of the region of the specific site by the tracking device for radiation treatment according to the present invention.

In order to use machine learning to detect the position of the region of the specific site, the discriminator is first learned. In this step of learning the discriminator, with the DRR image created at the time of treatment planning as an input layer and two-channel label images representing the region of the specific site specified at the time of the treatment planning as an output layer, a convolution layer used as the discriminator is learned by the machine learning. Then, the region of the specific site is detected. In this step of detecting the region of the specific site, with an X-ray fluoroscopic image as an input layer, two-channel label images indicating the position of the region of the specific site as an output layer are created by performing discrimination using the previously learned discriminator.

Figure 4:
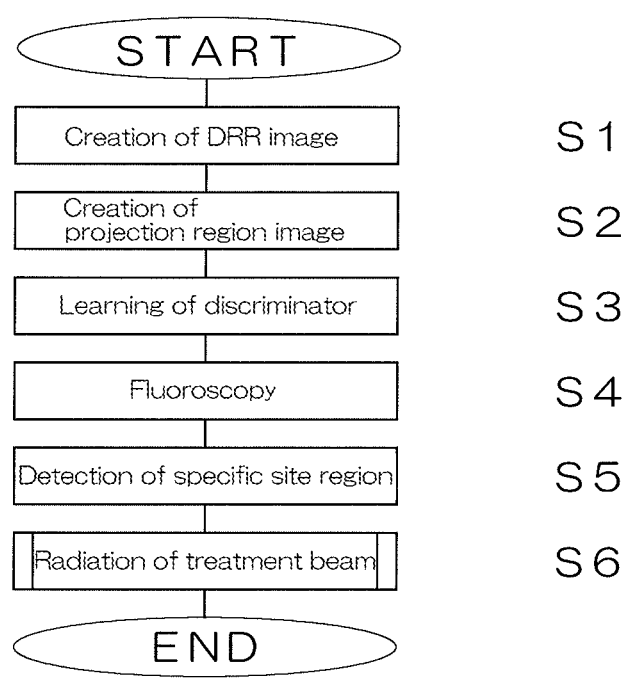
FIG. 4 is a flowchart illustrating a moving body tracking operation using the tracking device for radiation treatment according to the present invention.

Next, the moving body tracking operation including the detection of the position of the specific site by such steps will be described in detail. FIG. 4 is a flowchart illustrating the moving body tracking operation using the tracking device for radiation treatment according to the present invention. In addition, the following operation is performed using two X-ray imaging systems among the above-described first X-ray imaging system, second X-ray imaging system, third X-ray imaging system, and fourth X-ray imaging system; however, in the following, only one of them will be described. The following operation is performed in the same manner on the two X-ray imaging systems.

When performing the moving body tracking operation, before performing the X-ray fluoroscopy on the subject, the DRR image creation part 31 illustrated in FIG. 2 creates multiple DRR images including the specific site by performing the virtual fluoroscopic projection simulating geometrical fluoroscopic conditions between an X-ray tube 11 and a flat panel detector 21 on the four-dimensional CT image data created at the time of storing the treatment plan (Step S1). Note that the four-dimensional CT data created at the time of the treatment planning refers to the group of pieces of three-dimensional CT image data on the region including the specific site continuously imaged with time at the multiple continuous breathing phases at the time of storing the treatment plan.

Figure 5:
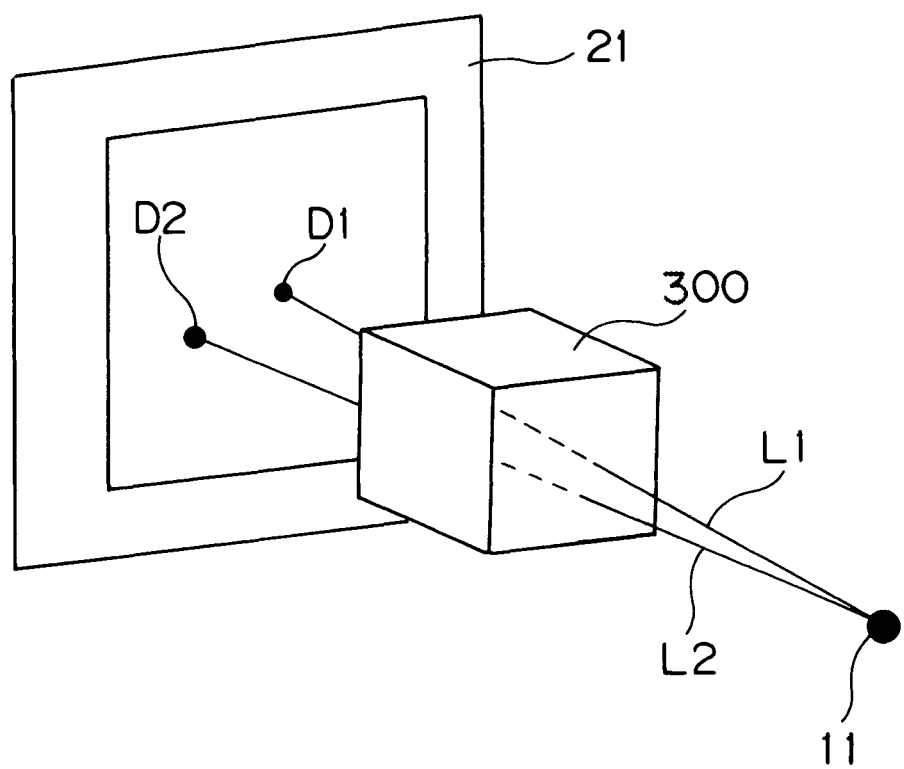
FIG. 5 is an explanatory view schematically illustrating a state where DRR images are created by virtual fluoroscopic projection simulating the geometrical fluoroscopic conditions between X-ray tubes 11 and flat panel detectors 21.

FIG. 5 is an explanatory view schematically illustrating a state where the DRR images are created by the virtual fluoroscopic projection simulating the geometrical fluoroscopic conditions between the X-ray tube 11 and the flat panel detector 21.

In FIG. 5, Reference Sign 300 represents CT image data. The CT image data 300 is one acquired from the treatment planning device 99, and three-dimensional voxel data as a set of multiple pieces of two-dimensional CT image data. The CT image data 300 has, for example a structure in which about 200 two-dimensional images having 512×512 pixels are stacked in a direction to cross the subject (in a direction along a line segment L1 or L2 illustrated in FIG. 5).

When creating a DRR image, the DRR image creation part 31 performs the virtual fluoroscopic projection on the CT image data 300. At this time, the three-dimensional CT image data 300 is arranged on a computer. Then, geometry that is the geometrical arrangement of the X-ray imaging system is reproduced on the computer. In this embodiment, on both sides, the X-ray tube 11 and flat panel detector 21 illustrated in FIG. 1 are arranged sandwiching the CT image data 300. The arrangement of the CT image data 300, the X-ray tube 11, and the flat panel detector 21 is the same geometry as the arrangement of the subject, the X-ray tube 11, and the flat panel detector 21 when performing fluoroscopy using the tracking device for radiation treatment illustrated in FIG. 1. Here, the geometry means the geometrical arrangement relationship among the imaging object, the X-ray tube 11, and the flat panel detector 21.

In this state, a large number of line segments L connecting the X-ray tube 11 and respective pixels of the flat panel detector 21 via respective pixels of the CT-image data 300 are set. In addition, for convenience of description, FIG. 5 illustrates the two line segments L1, L2. Further, on each of the line segments L, multiple calculation points are set. Then, a CT value at each calculation point is calculated. When calculating the CT value, interpolation using CT values in CT data voxels around the calculation point is performed. After that, CT values at respective calculation points on each of the line segments L are accumulated. The resulting accumulated value is converted to the line integral of a linear attenuation coefficient to calculate X-ray attenuation, and thereby a DRR image is created.

At the time of creating the DRR image, the DRR image is created with parameters, which include at least one of a projection coordinate and an angle and are for creating the DRR image, changed with respect to the CT image data 300. Alternatively, image processing including at least one of slight translation, rotation, deformation, and scaling is performed. The reason to perform the translation, rotation, deformation, and/or scaling is to make it possible to more surely track the specific site even when the specific site of the subject, such as a tumor, makes unreproducible movements or is deformed in the body of the subject with respect to the CT image data 300.

In addition, the frame rate of the CT image data 300 serving as a base for the DRR image is smaller than the frame rate of the X-ray fluoroscopic image; however, by changing the parameters for creating the DRR image, the specific site between frames of DRR images can be simulated to more accurately detect the region of the specific site. Also, the X-ray fluoroscopic image is a transmission image, and therefore high contrast backgrounds such as bone regions and/or the diaphragm are imaged superimposed on the region of the specific site. In contrast, when changing the parameters as described above, how the backgrounds are superimposed on the specific site is variously changed, and therefore by learning it, the superimposition of the backgrounds can be neglected to more surely discriminate the specific site.

In addition, at least one of contrast change, noise addition, and edge enhancement is performed on the created DRR image. The reason to perform the contract change, the noise addition, and/or the edge enhancement is to make it possible to more surely track the specific site by absorbing the difference in image quality between the DRR image and the X-ray image.

The above-described changes in parameters for DRR image creation, such as a projection coordinate and an angle or the contrast change, noise addition, and/or edge enhancement are performed randomly within predetermined ranges or in a mode in which various changes are made at regular intervals. In doing so, a large number of DRR images can be created from CT image data 300 on one patient. For this reason, a custom-made discriminator corresponding to each patient can be learned using a large number of DRR images created as described. In addition, a discriminator can also be learned using DRR images of a large number of patients.

Next, a projection region image representing the region of the specific site is created by performing the virtual fluoroscopic projection simulating the geometrical fluoroscopic conditions between the X-ray tube 11 and the flat panel detector 21 with respect to the subject on the region of the specific site registered on the CT image data on the region including the specific site at the time of the treatment planning (Step S2). The projection region image representing the region of the specific site will be used as a training label image at the time of the machine learning.

At this time as well, as in the case illustrated in FIG. 5, the virtual fluoroscopic projection is performed on the region of the specific site. At the time of creating the projection region image representing the region of the specific site as well, the projection region image is created with parameters for creating the projection region image, such as a projection coordinate and an angle, changed with respect to the region of the specific site. That is, slight translation, rotation, deformation, and/or scaling are performed. In addition, at the time of creating the projection region image, the parameters including the projection coordinate and the angle among the geometrical fluoroscopic conditions are changed under the same conditions as those at the time of the above-described DRR image creation, or image processing including the rotation, deformation, and/or scaling of the image is performed under the same conditions. In doing so, as described above, even when the specific site of the subject, such as a tumor, makes unreproducible movements or is deformed in the body of the subject with respect to the CT image data 300, the specific site can be more surely tracked.

Figure 6:
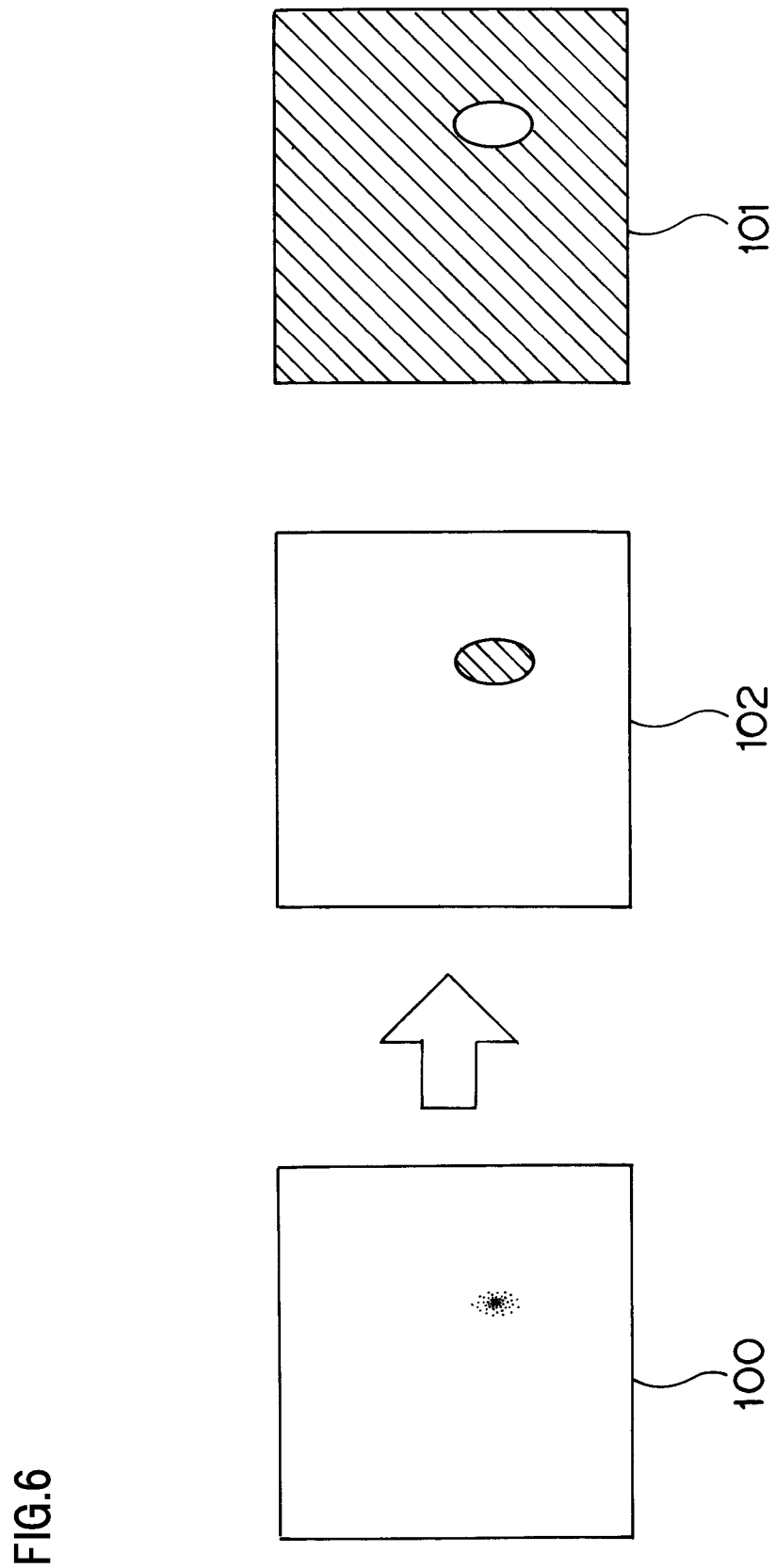
FIG. 6 is a schematic diagram illustrating a DRR image 100 and label images 101, 102 that are images of a projection region representing the region of a specific site.

FIG. 6 is a schematic diagram illustrating a DRR image 100 and label images 101, 102 that are images of a projection region representing the region of the specific site.

The projection region images representing the region of the specific site are the two (two-channel) label images 101, 102. Here, the label image 101 is a background label image representing a region other than the specific site. Also, the label image 102 is a specific site label image representing the region of the specific site.

After the end of the above steps, the machine learning is performed with the DRR image 100 as an input layer and the two-channel label images 101,102 as an output layer, and thereby the discriminator for recognizing the region of the specific site is learned (Step S3).

A method for pixel-based classification (labelling) into classes to which respective pixels belong is called semantic segmentation. As a highly accurate and high-speed semantic segmentation method, FCN (Fully Convolutional Networks) is known. A convolutional neural network used in FCN is configured as in, for example, FIG. 3. That is, when learning the discriminator, the input layer corresponds to the DRR image, and the output layer corresponds to the two-channel label images 101, 102 illustrated in FIG. 6. A channel-1 label image is the background label image, and a channel-2 label image is the specific site label image. That is, respective pixel values of each channel label image 101, 102 are values corresponding to probabilities at which the respective pixels of the input image belong to the respective classes. An intermediate layer is configured of only a convolution layer serving as the discriminator, and the parameters are determined by learning.

Note that in the above-described embodiment, the two-channel label images 101, 102 are created; however, since the image is only divided into the background and the specific site, a label image may be set to be of one channel. Alternatively, in an opposite manner, in the case of breathing phase-based classification into the background and the specific site, n channels larger in number than the two channels may be used. For example, when using the present invention for discriminating a prosthetic joint or a treatment beam radiation prohibition organ, or the like, it is only necessary to perform classification into n classes and create n-channel label images.

The above work can be preliminarily performed before the radiation treatment. For this reason, it is not necessary to create templates just before radiation treatment as in the conventional case of using template matching. Accordingly, without temporally restraining the subject, the throughput of radiation treatment can be improved.

In addition, when performing the above-described machine learning, the ratio of the specific site in the DRR image 100 is small, and in the label images 101, 102 as training label images, most of the image area serves as a background label. For this reason, a loss function at the time of learning the discriminator is determined with the degree of coincidence of the background label as a main factor. As a result, learning like discriminating the entire image as a background label with a specific site label neglected may be performed, and in such a case, a specific site has not been able to be detected.

Therefore, it is conceivable that the specific site label can also be discriminated by performing the learning with the weight of the specific site label increased when calculating the loss function in the machine learning. However, if such a configuration is employed, a ratio at which the background label contributes to the loss function is decreased, and therefore discrimination learning of the background label becomes insufficient, which may erroneously determine the background part as the specific site even after the learning is advanced.

In order to respond to such a problem, it is preferable to employ a configuration in which the weighting of the specific site label is sequentially decreased in accordance with the degree of progress of the learning. That is, the discriminator learning part 33 first increases the weight of the specific site label at the time of calculating the loss function on the basis of the ratio in area between the specific site label and the background label in the training label images (the ratio in the area of the hatching region between the label image 102 and the label image 101 in FIG. 6), and learns the discriminator. Then, the weight of the specific site label is gradually decreased in accordance with the degree of progress of learning the discriminator. The degree of progress of learning the discriminator at this time is determined on the basis of, for example, the number of times of repeating the learning.

Figure 7:
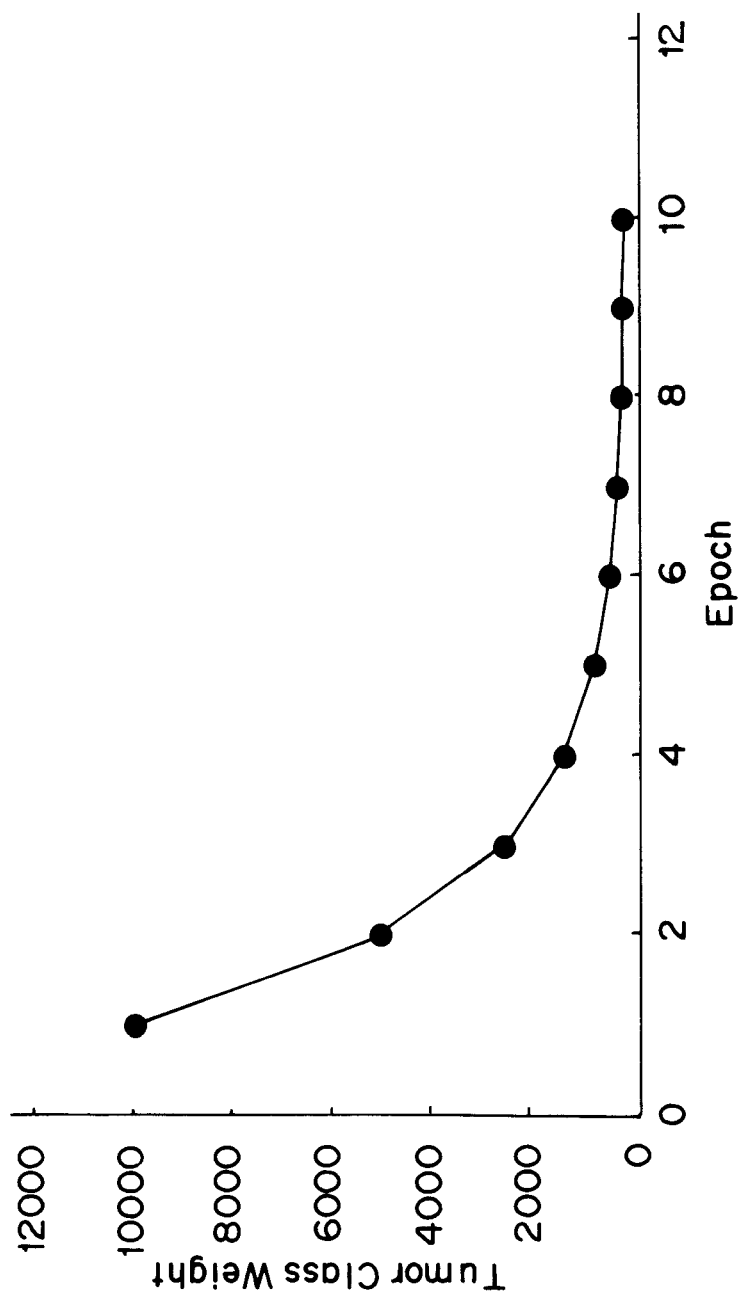
FIG. 7 is a graph illustrating the relationship between the weight of a specific site label and the number of times of repetition.

FIG. 7 is a graph illustrating the relationship between the weight of the specific site label and the number of times of repetition. In this graph, the vertical axis represents weight for the specific site (tumor) and the horizontal axis represents an epoch indicating the number of times of repetition. Here, the epoch refers to a unit in which learning is performed by repeating one training data set several times.

As illustrated in this graph, the weight of the specific site is set to, for example, 10000 on the basis of the ratio in area between the specific site label and the background label. Then, the weight is decreased as the learning is repeated, and finally converged to 1 or more (e.g., about 20).

By employing such a configuration, when calculating the loss function in the machine learning, the specific site label and the background label in the training label images can be equivalently handled and the specific site can be more surely detected. In addition, in the former half of the learning, the discriminator is learned so that the specific site can be surely detected, and in the latter half of the learning, the learning is performed so as to prevent the background part from being erroneously determined, so that the discriminator satisfying both the detection reliability of the specific site and the suppression of the erroneous detection can be learned.

In addition, instead of the number of times of repetition, a configuration in which from a decrease in the value of the loss function, it is determined that the learning has advanced, and the weight is decreased as the learning advances may be employed.

Also, when performing the above-described machine learning, it is difficult to determine whether the boundary region between the specific site label and the background label belongs to the specific site or the background, and therefore a discrimination result after the machine learning may be erroneous in determination. For this reason, the discriminator learning part 33 preferably employs a configuration to, when calculating the loss function for performing the machine learning, weight a loss function for an image obtained by trimming the periphery of the specific site and add the resulting loss function to the loss function for the entire image.

Figure 8:
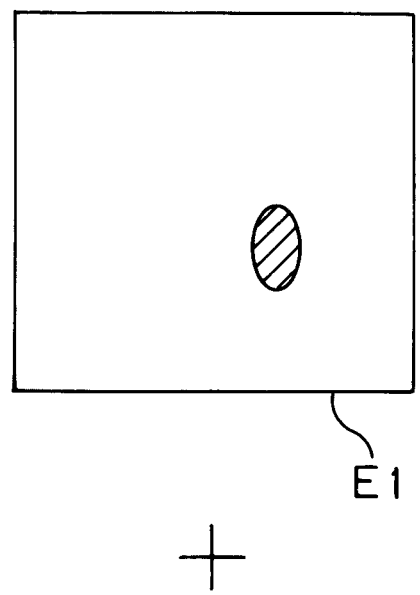
FIG. 8 is an explanatory diagram schematically illustrating a weighting range.
Figure 8:
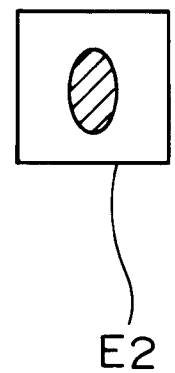

FIG. 8 is an explanatory diagram schematically illustrating a weighting range.

The discriminator learning part 33 weights a loss function for an area E2 of an image obtained by trimming the periphery of the specific site and adds the resulting loss function to the loss function for an area E1 corresponding to the entire image when calculating the loss function for performing the machine learning.

By employing such a configuration, the weight of the vicinity of a difficult-to-discriminate boundary between the specific site label and the background label can be increased to perform the learning, and this makes it possible to suppress the erroneous determination of the vicinity of the boundary between the specific site label and the background label and more surely detect the specific site.

After learning the discriminator in the above steps, the X-ray fluoroscopy is then started on the subject (Step S4).

Subsequently, the specific site region is detected by performing discrimination using the previously leaned discriminator (convolution layer) (Step S5). That is, the previously learned discriminator is used for a fluoroscopic image obtained by the X-ray fluoroscopy at a predetermined frame rate to output two-channel label images as an output layer. That is, a region where the probability of the specific site is large is recognized in an X-ray fluoroscopic image of each frame.

Figure 9:
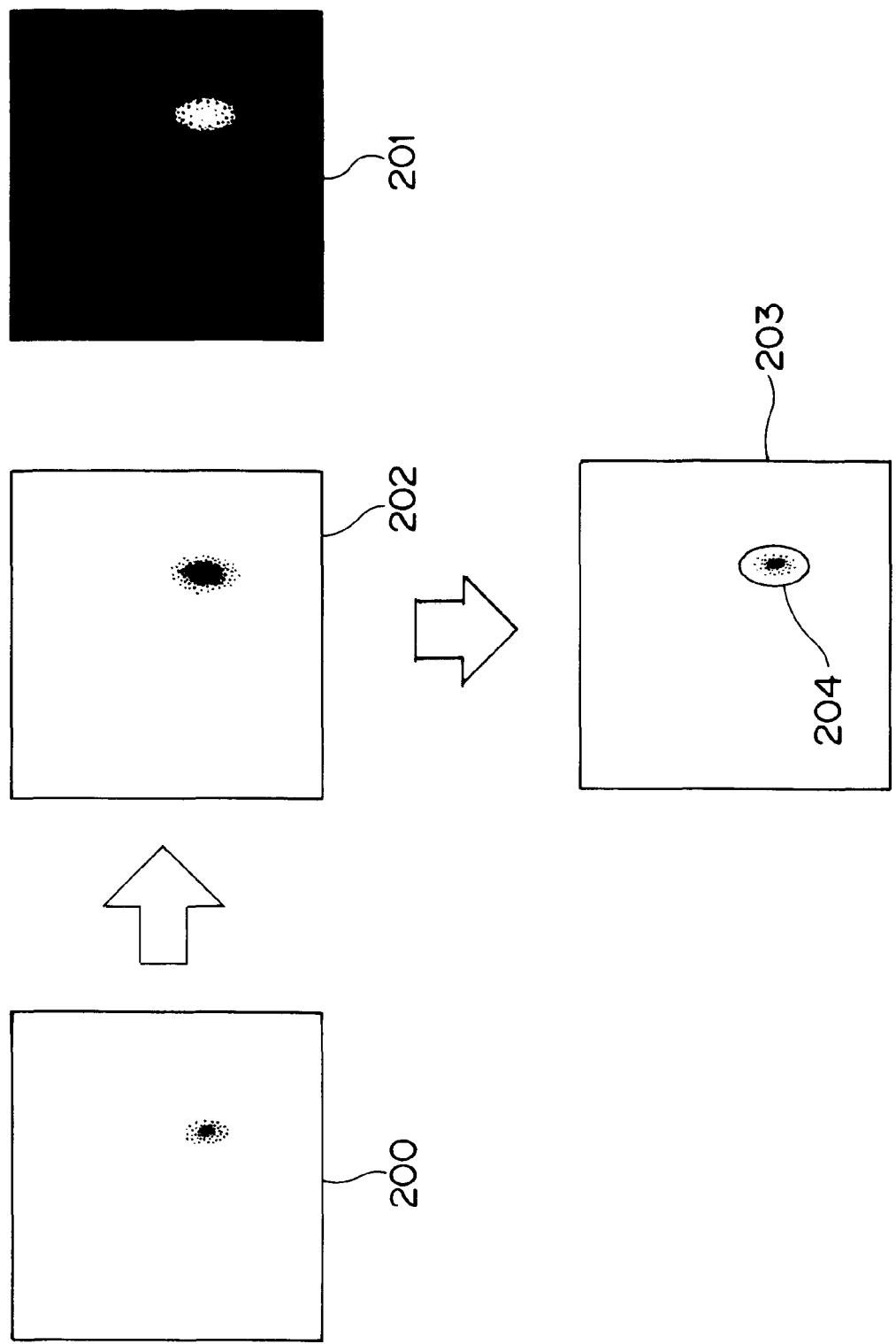

FIG. 9 is a schematic diagram illustrating an X-ray fluoroscopic image 200, label images 201, 202 representing the region of the specific site, and the like.

As illustrated in the diagram, by performing discrimination using the previously learned discriminator for the X-ray fluoroscopic image 200, the two-channel label images, i.e., the background label image 201 and the specific site label image 202 are created. The two-channel label images are created for an X-ray fluoroscopic image 200 of each frame. Then, the specific site region 204 is determined, and an image 203 in which a display representing the specific site region 204 and the fluoroscopic image are superimposed is created.

In addition, when determining the specific site region 204, it is only necessary to provide a predetermined threshold value for probabilities of label images, and as the specific site region 204, determine regions whose probabilities exceed the threshold value. At this time, the smoothing of the boundary and the deletion/integration of minute regions may be performed using a morphological operation or the like. In addition, when the difference from a tumor shape expected from CTV (clinical target volume) is large, the radiation of the treatment beam may be stopped as an error. Further, the specific site region 204 is not required to correspond to the entire CTV area, and only part of the CTV area, such as the vicinity of the center of CTV, may be specified, and a certain region with the part as the center of gravity may be determined as the specific site region 204. At this time, the specific site region 204 may be determined by using CTV created at the time of the treatment planning to match the center of gravity in a label image with the center of gravity of the CTV created at the time of the treatment planning.

A sliding window in CNN requires the forward propagation calculation of CNN every time a detection window is slid, and in a region where slid detection windows overlap each other, a redundant convolution operation is performed, and therefore real-time image processing is difficult. On the other hand, in FCN, the entire label image can be obtained for the entire input image or the entire search region by performing the forward propagation calculation once, and therefore the shape of the specific site can be recognized in real time.

When during performing the X-ray fluoroscopy, the region of the specific site can be detected in the resulting X-ray fluoroscopic image, the treatment beam is radiated by the irradiation device 90 (Step S6). That is, only when the position of the specific site region 204 coincides with a specific position at a specific phase among breathing phases of the subject, the treatment beam is radiated to provide radiation treatment.

Figure 10:
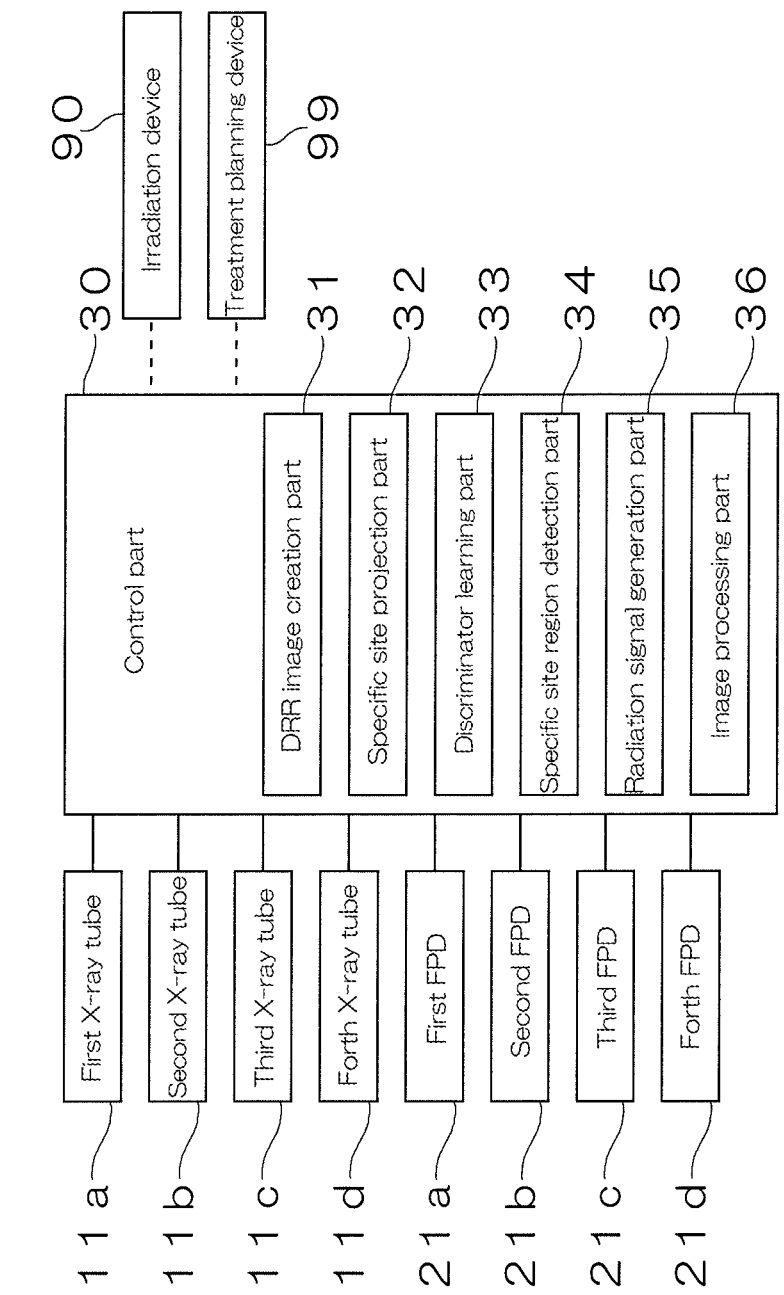
FIG. 10 is a block diagram illustrating a main control system of a tracking device for radiation treatment according to a second embodiment of the present invention.
Figure 11:
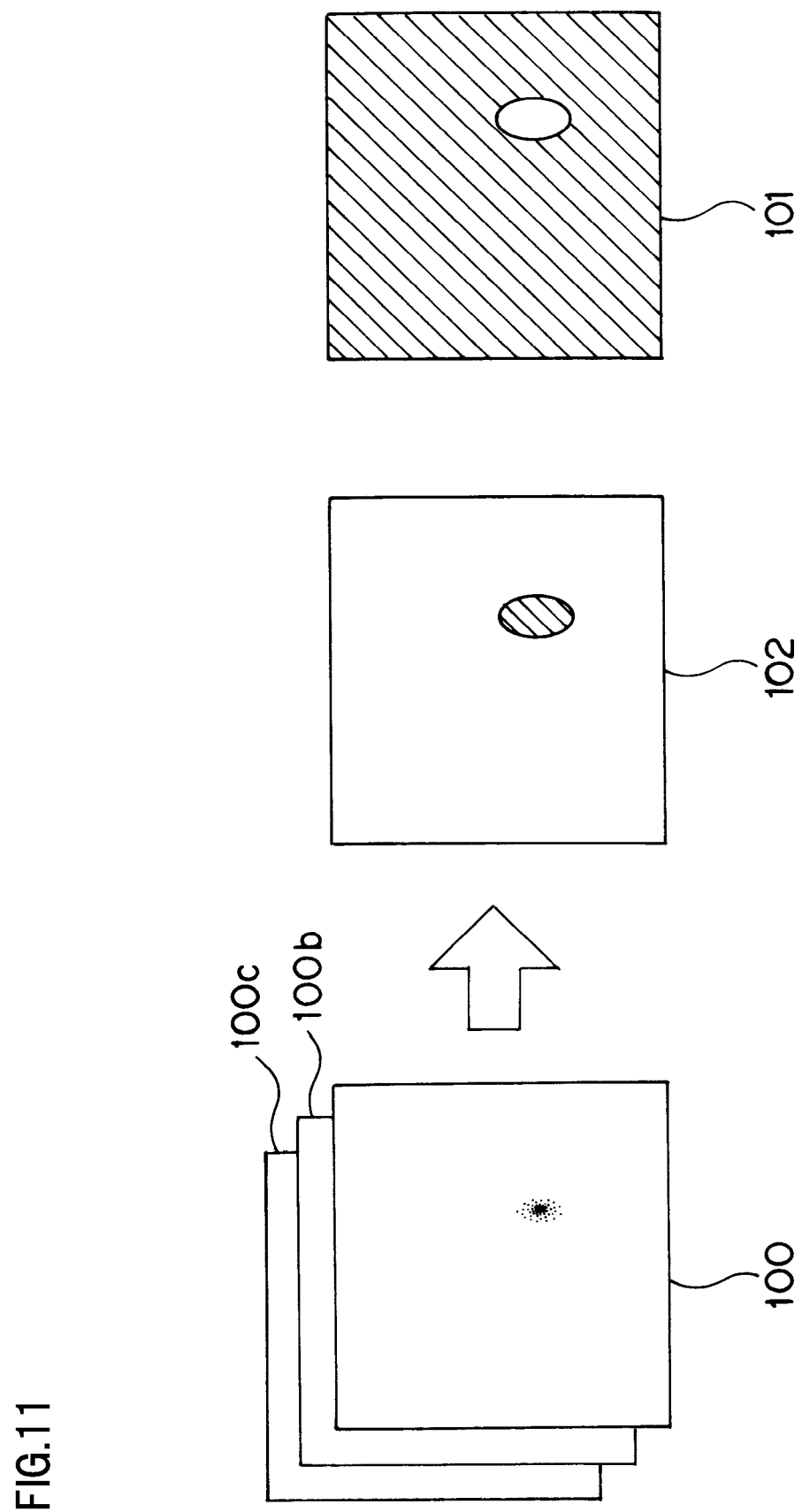
FIG. 11 is a schematic diagram illustrating a DRR image 100, images 100b, 100c after image processing of it, and label images 101, 102 that are images of a projection region representing the region of a specific site.

Next, a second embodiment of the present invention will be described. FIG. 10 is a block diagram illustrating a main control system of a tracking device for radiation treatment according to the second embodiment of the present invention. FIG. 11 is a schematic diagram illustrating a DRR image 100, images 100b, 100c after image processing of it, and label images 101, 102 that are images of a projection region representing a region of a specific site. FIG. 12 is a schematic diagram illustrating an X-ray fluoroscopic image 200, images 200b, 200c after image processing of it, label images 201, 202 representing the region of the specific site, and the like.

In the tracking device for radiation treatment according to the second embodiment, a control part 30 includes an image processing part 36 that creates the images 100b, 100c after the image processing of the DRR image 100, like an image 100b and an image 100c respectively obtained by performing edge enhancement and frequency division on the DRR image 100 illustrated in FIG. 6, as well as creates the images 200b, 200c after the image processing of the X-ray fluoroscopic image 200, like an image 200b and an image 200c respectively obtained by performing edge enhancement and frequency division on the X-ray fluoroscopic image 200 illustrated in FIG. 9.

In the above-described embodiment, as illustrated in FIG. 6, the machine learning is performed with the DRR image 100 as an input layer and the two-channel label images 101, 102 as an output layer. On the other hand, in the second embodiment, as illustrated in FIG. 11, machine learning is performed with the DRR image 100 and the images 100b, 100c after the image processing of it as an input layer and the two-channel label images 101, 102 as an output layer. In addition, in the above-described embodiment, as illustrated in FIG. 9, the two-channel label images, i.e., the background label image 201 and the specific site label image 202 are created by using the previously learned discriminator to perform discrimination on the X-ray fluoroscopic image 200. On the other hand, in the second embodiment, as illustrated in FIG. 12, the two-channel label images, i.e., the background label image 201 and the specific site label image 202 are created by using a previously learned discriminator to perform discrimination on the X-ray fluoroscopic image 200 and the images 200b, 200c after the image processing of it. In addition, the image processing part 36 perform image processing under the same conditions, i.e., the same image processing on the DRR image and the X-ray fluoroscopic image.

When employing such a configuration, the machine learning is performed using not only the DRR image 100 but also the images after the image processing of the DRR image 100, and therefore the discriminator with higher accuracy can be created. Further, with use of this discriminator, the discrimination is performed using not only the X-ray fluoroscopic image 200 but the images after the image processing of the X-ray fluoroscopic image 200, and therefore the region of the specific site can be more accurately detected.

As described, according to the tracking device for radiation treatment and method for tracking a moving body according to the present invention, since a convolution layer to be used as a discriminator is learned by machine learning with DRR images created at the time of treatment planning as an input layer and two-channel label images representing the region of a specific site specified at the time of the treatment planning as an output layer, and then the region of the specific site as an output layer is positionally recognized by performing discrimination using the previously learned discriminator with X-ray fluoroscopic images as an input layer, it is possible to detect the position of the specific site or track the specific site in real time.

In addition, in the above-described embodiments, an X-ray fluoroscopic image may be blurred by a Gaussian filter or the like and then inputted to the discriminator. In general, a DRR image is created from a low-resolution CT image, and is therefore low in resolution as compared with an X-ray fluoroscopic image. For this reason, the specific site can be more surely discriminated by blurring an X-fluoroscopic image to reduce the resolution of the X-ray fluoroscopic image to a resolution equivalent to that of a DRR image at the time of learning while reducing noise.

Also, in the above-described embodiments, a DRR image and an X-ray fluoroscopic image to be inputted to the discriminator may be subjected to contrast normalization in advance and then inputted. In addition, a local contrast normalization layer or a local response normalization layer may be added to the intermediate layer.

Further, in the above-described embodiments, the discriminator is learned with the projection region images representing the region of the specific site created by the specific site projection part 32 as the training label images; however, other training label images may be used as long as they are images representing the region of the specific site.

In addition, in the above-described embodiments, described is the tracking device for radiation treatment, which tracks the movement of the specific site in order to radiate the treatment beam to the specific site; however, the present invention can also be applied in the same manner to a position detection device that detects the position of the specific site on the basis of X-ray fluoroscopic images including the specific site of the subject.

REFERENCE SIGNS LIST

11a First X-ray tube
11b Second X-ray tube
11c Third X-ray tube
11d Fourth X-ray tube
21a First flat panel detector
21b Second flat panel detector
21c Third flat panel detector
21d Fourth flat panel detector
30 Control part
31 DRR image creation part
32 Specific site projection part
33 Discriminator learning part
34 Specific site region detection part
35 Radiation signal generation part
90 Irradiation device
99 Treatment planning device

The invention claimed is:

1. A tracking device for radiation treatment that collects an X-ray fluoroscopic image including a specific site of a subject, detects a position of the specific site, and tracks a movement of the specific site, the tracking device comprising:
a DRR image creation part that creates a DRR image including the specific site by performing virtual fluoroscopic projection simulating geometrical fluoroscopic conditions between an X-ray tube and an X-ray detector with respect to the subject on CT image data on a region including the specific site, the CT image data being created at a time of treatment planning, and the specific site being a site at which a treatment beam is irradiated;
a discriminator learning part that learns a discriminator by performing machine learning, with the DRR image created by the DRR image creation part as an input layer and a training label image indicating the region of the specific site as an output layer; and
a specific site region detection part that detects the region of the specific site by performing discrimination using the discriminator learned by the discriminator learning part on the X-ray fluoroscopic image including the specific site.

2. The tracking device for radiation treatment according to claim 1, the tracking device further comprising
a specific site projection part that creates a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at the time of the treatment planning, wherein
the discriminator learning part learns the discriminator with the projection region image representing the region of the specific site as the training label image, the projection region image being created by the specific site projection part.

3. The tracking device for radiation treatment according to claim 2, wherein
the DRR image creation part creates the DRR image with parameters including at least one of a projection coordinate and an angle among the geometrical fluoroscopic conditions changed or image processing including at least one of rotation, deformation, and scaling of an image performed,
the specific site projection part creates the projection region image representing the region of the specific site parameters including at least one of a projection coordinate and an angle among the geometrical fluoroscopic conditions changed or image processing including at least one of rotation, deformation, and scaling of an image performed, and
the DRR image creation part and the specific site projection part change parameters including at least one of a projection coordinate and an angle among the geometrical fluoroscopic conditions under a same condition, or perform image processing including at least one of rotation, deformation, and scaling of an image under a same condition.

4. The tracking device for radiation treatment according to claim 2, wherein
the DRR image creation part performs at least one of contrast change, noise addition, and edge enhancement on the created DRR image.

5. The tracking device for radiation treatment according to claim 2, wherein
the discriminator is a neural network configured of a convolution layer of the input layer and the output layer.

6. The tracking device for radiation treatment according to claim 2, wherein
when calculating a loss function for performing the machine learning, the discriminator learning part performs the calculation after increasing weight of a specific site label on a basis of areas of a specific site label and a background label in the training label image, and then performs the calculation while sequentially decreasing the weight of the specific site label as the learning progresses.

7. The tracking device for radiation treatment according to claim 2, wherein
when calculating a loss function for performing the machine learning, the discriminator learning part weights a loss function for an image obtained by trimming a periphery of the specific site and adds a resulting loss function to a loss function for an entire image.

8. The tracking device for radiation treatment according to claim 2, the tracking device further comprising
an image processing part that performs image processing of the DRR image and the X-ray fluoroscopic image, wherein
the discriminator learning part performs the machine learning with use of the DRR image and a DRR image after the image processing by the image processing part, and
the specific site region detection part performs the discrimination using the discriminator learned by the discriminator learning part on the X-ray fluoroscopic image including the specific site and an X-ray fluoroscopic image that includes the specific site and was subjected to the image processing by the image processing part under a same condition as for the DRR image.

9. A position detection device that detects a position of a specific site on a basis of an X-ray fluoroscopic image including the specific site of a subject, the position detection device comprising:
a DRR image creation part that creates a DRR image including the specific site by performing virtual projection simulating geometrical fluoroscopic conditions between an X-ray tube and an X-ray detector with respect to the subject on CT image data on a region including the specific site;

a discriminator learning part that learns a discriminator by performing machine learning, with the DRR image created by the DRR image creation part as an input layer and a training label image indicating the region of the specific site as an output layer; and a specific site region detection part that detects the region of the specific site by performing discrimination using the discriminator learned by the discriminator learning part on the X-ray fluoroscopic image including the specific site.

10. The position detection device according to claim 9, further comprising a specific site projection part that creates a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at a time of treatment planning, wherein the discriminator learning part learns the discriminator with the projection region image representing the region of the specific site as the training label image, the projection region image being created by the specific site projection part.

11. The position detection device according to claim 10, wherein the DRR image creation part creates the DRR image with parameters including at least one of a projection coordinate and an angle among the geometrical fluoroscopic conditions changed or image processing including at least one of rotation, deformation, and scaling of an image performed, the specific site projection part creates the projection region image representing the region of the specific site with parameters including at least one of a projection coordinate and an angle among the geometrical fluoroscopic conditions changed or image processing including at least one of rotation, deformation, and scaling of an image performed, and the DRR image creation part and the specific site projection part change parameters including at least one of a projection coordinate and an angle among the geometrical fluoroscopic conditions under a same condition, or perform image processing including at least one of rotation, deformation, and scaling of an image under a same condition.

12. The position detection device according to claim 10, wherein the DRR image creation part performs at least one of contrast change, noise addition, and edge enhancement on the created DRR image.

13. The position detection device according to claim 10, wherein the discriminator is a neural network configured of a convolution layer of the input layer and the output layer.

14. The position detection device according to claim 10, wherein when calculating a loss function for performing the machine learning, the discriminator learning part performs the calculation after increasing weight of a specific site label on a basis areas of a specific site label and a background label in the training label image, and then performs the calculation while sequentially decreasing the weight of the specific site label as the learning progresses.

15. The position detection device according to claim 10, wherein when calculating a loss function for performing the machine learning, the discriminator learning part weights a loss function for an image obtained by trimming a periphery of the specific site and adds a resulting loss function to a loss function for an entire image.

16. The position detection device according to claim 10, further comprising an image processing part that performs image processing of the DRR image and the X-ray fluoroscopic image, wherein the discriminator learning part performs the machine learning with use of the DRR image and a DRR image after the image processing by the image processing part, and the specific site region detection part performs the discrimination using the discriminator learned by the discriminator learning part on the X-ray fluoroscopic image including the specific site and an X-ray fluoroscopic image that includes the specific site and was subjected to the image processing by the image processing part under a same condition as for the DRR image.

17. A method for tracking a moving body, the method collecting an X-ray fluoroscopic image including a specific site of a subject, detecting a position of the specific site, and tracking a movement of the specific site, the method comprising:

a DRR image creation step of creating a DRR image including the specific site by performing virtual fluoroscopic projection simulating geometrical fluoroscopic conditions between an X-ray tube and an X-ray detector with respect to the subject on CT image data on a region including the specific site, the CT image data being created at a time of treatment planning, and the specific site being a site at which a treatment beam is irradiated;

a specific site projection step of creating a projection region image representing the region of the specific site by performing the virtual fluoroscopic projection simulating the geometrical fluoroscopic conditions between the X-ray tube and the X-ray detector with respect to the subject on the region of the specific site registered on the CT image data on the region including the specific site at the time of the treatment planning;

a discriminator learning step of learning a discriminator by performing machine learning with the DRR image created in the DRR image creation step as an input layer and the projection region image created in the specific site projection step as an output layer; and a specific site region detection step of detecting the region of the specific site by performing discrimination using the discriminator learned in the discriminator learning step on the X-ray fluoroscopic image including the specific site, the X-ray fluoroscopic image being obtained by detecting an X-ray passing through the subject after radiation from the X-ray tube with use of the X-ray detector.

* * * * *